United States Patent [19]

Hayler et al.

[11] Patent Number: 5,777,128
[45] Date of Patent: Jul. 7, 1998

[54] PROCESS FOR PREPARING BENZOPYRAN COMPOUNDS

[75] Inventors: John David Hayler, East Grinstead; Trevor John Grinter, Rotherfield, both of United Kingdom; Vance Novak, Devon, Pa.; Norman John Lewis, Tunbridge Wells, United Kingdom

[73] Assignee: SmithKline Beecham p.l.c., Brentfor, England

[21] Appl. No.: 737,661

[22] PCT Filed: May 18, 1995

[86] PCT No.: PCT/EP95/01915

§ 371 Date: Nov. 21, 1996

§ 102(e) Date: Nov. 21, 1996

[87] PCT Pub. No.: WO95/32199

PCT Pub. Date: Nov. 30, 1995

[30] Foreign Application Priority Data

May 21, 1994 [GB] United Kingdom ............. 9410207

[51] Int. Cl.[6] ................................. C07D 257/04
[52] U.S. Cl. .......................... 548/252; 548/253
[58] Field of Search .......................... 548/252, 253

[56] References Cited

U.S. PATENT DOCUMENTS

| 4,159,273 | 6/1979 | Brown et al. ............ 260/345.5 |
| 5,597,929 | 1/1997 | Ushio et al. ............ 548/253 |

FOREIGN PATENT DOCUMENTS

WO 94/12492  6/1994  WIPO .

OTHER PUBLICATIONS

Kakai et al., New Potent Antagonist of Leukotrienes, J. Med. Chem., 31(1), 84–91, 1988.
Chemical Abstracts, vol. 115, No. 17, 1991, p874, col. 2, abstract 182817v.

Primary Examiner—Joseph McKane
Attorney, Agent, or Firm—James M. Kanagy; Stephen Venetianer; Edward T. Lentz

[57] ABSTRACT

The present invention relates to a process for preparing compounds of structure (I), and the intermediate compound of formula (II).

3 Claims, No Drawings

PROCESS FOR PREPARING BENZOPYRAN COMPOUNDS

This application is a 371 of PCT/EP95/01915 filed May 18, 1995.

The present invention relates to a process for preparing certain substituted benzopyran compounds which are useful as intermediates in the preparation of a class of substituted benzopyran compounds known in the art as therapeutic agents.

Substituted benzopyran compounds are known in the art. For example EP 0 173 516-A discloses a class of substituted benzopyran compounds which are described as compounds having activity as leukotriene antagonists and 5-α-reductase inhibitors and useful in therapy in the treatment of diseases caused or exacerbated by leukotrienes or 5-α-reductase activity.

The present invention relates to a method for preparing key intermediates used in the preparation of a particular sub-class of the compounds disclosed in EP 0 173 516-A, in particular compounds of the structure (A):

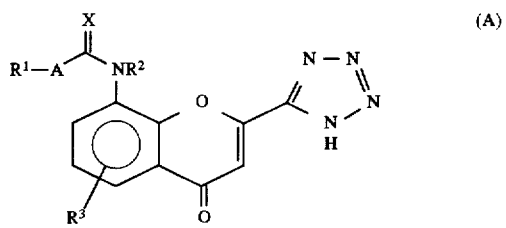

in which, $R^1$ is $C_{1-20}$alkyl, $C_{2-20}$alkenyl, $C_{2-20}$alkynyl, or a group of structure:

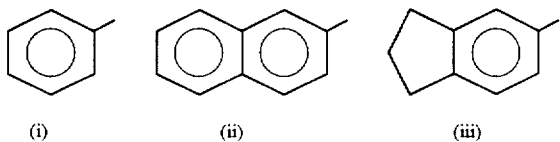

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s); $R^2$ is hydrogen or $C_{1-6}$alkyl; $R^3$ is hydrogen, halogen, hydroxy, nitro, a group of general formula —$COOR^4$ (wherein $R^4$ represents hydrogen or $C_{1-6}$alkyl), $C_{1-6}$alkyl, $C_{1-6}$alkoxy or $C_{1-6}$alkylthio; A is a single bond or a methylene, ethylene, trimethylene, tetramethylene, vinylene, propenylene, butenylene, butadienylene or ethynylene group optionally being substituted by one, two or three $C_{1-10}$alkyl and/or phenyl group(s); and X is oxygen or sulphur.

Known procedures for preparing such compounds of structure (A) include a final step reaction in which the intermediate (B) (in which R is tetrazol-5-yl) is reacted with an activated intermediate such as (C) to form the desired compounds (A):

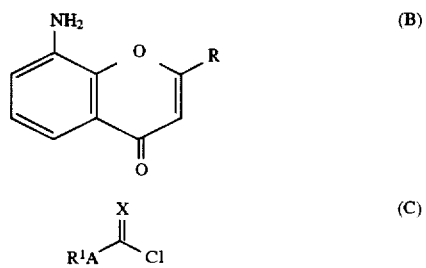

The compounds of structure (B) are prepared via procedures described in EP 0 173 516-A in which the benzopyran ring is formed first and then the tetrazole ring prepared via conversion from the corresponding compound B in which R is a carboxylic acid group, via the amide and nitrile group using standard chemistry techniques.

The present invention provides an improved route to the intermediates of structure (B) (and closely related compounds).

In a first aspect is therefore provided a process for the preparation of a compound of structure (I):

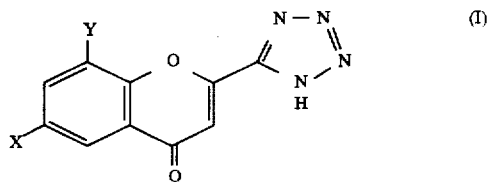

in which Y is $NO_2$, $NH_2$ or Y is $NO_2$, $NH_2$ or NHacetyl, $N(Bn)_2$, CO(Tet) where Tet is a tetrazol-5-yl group,

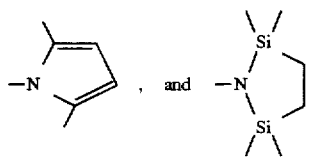

and X is hydrogen or halogen, which process comprises cyclisation of a compound of structure (II):

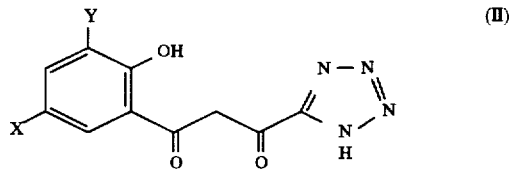

in which X and Y are as described for structure (I).

Suitably, the reaction is carried out at reflux temperature in a $C_{1-4}$alkanol solvent, in the presence of a suitable acid. Preferably, the reaction is carried out at reflux temperature in methanol as a solvent in the presence of concentrated hydrochloric acid or concentrated sulphuric acid.

Suitable amine protecting groups Y will be apparent to those skilled in the art, and include, for example, NHacetyl, $N(Bn)_2$, CO(Tet) where Tet is a tetrazol-5-yl group.

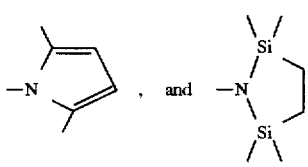

It will be appreciated that compounds of formula (II) can exist as salts, for example as the sodium salt. Compounds of formula (II) can also exist in different tautomeric forms. Salt and tautomeric forms of compounds of formula (II) can be used in the above process and form an aspect of the invention.

The compounds of structure (II) can be prepared by standard techniques or, alternatively, by rearrangement of compounds of structure (III):

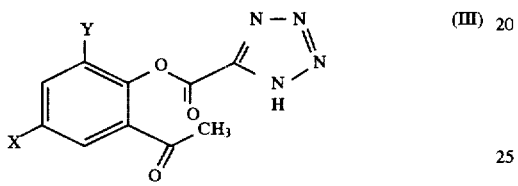

in which X and Y are as described for structure (I).

As will be apparent to those skilled in the art, the rearrangement of the compounds (III) is known as a Baker-Venkataraman rearrangement.

In particular, the reactions claimed herein are useful in the preparation of compounds (I) in which Y is $NH_2$ or $NO_2$ and X is hydrogen. It will, of course, be appreciated that compounds of structure (I) in which Y is $NO_2$ can be converted to compounds (I) in which Y is $NH_2$ by standard techniques. Furthermore, where an amine protecting group has been used, it can, of course, be removed using techniques well known to those in the art. In addition, the rearrangement reaction can be carried out on compounds of structure (III) in which Y is

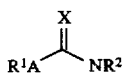

in which $R^1$, $R^2$, A and X are as described for structure (A), to form the compounds (II) in which Y is

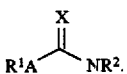

Such intermediates can then be cyclised direct to the desired compounds of structure (A) using the methods described in co-pending PCT Application No. PCT/EP 93/03257 filed Nov. 19, 1993.

The following examples serve to illustrate the invention.

EXAMPLE 1

Preparation of 8-amino-4-oxo-2-(tetrazol-5-yl)-4H-1-benzopyran

Method A

A solution of 1,1,1,3,3,3-hexamethyldisilazane (6.8 ml, 6.8 eq) in anhydrous THF (100 ml) was cooled to −78° C. under an atmosphere of nitrogen. The resulting solution was then treated with dropwise addition of 2.5M butyl lithium (12.97 ml, 6.8 eq), keeping the temperature <−40° C. After complete addition the solution was allowed to warm to ambient then re-cooled to −78° C. The re-cooled solution was then treated with a solution of the 3-N-acetylamino-2-hydroxyacetophenone (0.92 g, 1 eq), tetrazole-ester, (0.75 g, 1.1 eq) in (10 ml) of anhydrous THF keeping the temperature <−40° C. After complete addition the reaction was allowed to warm to ambient and stirred at this temperature for 18hrs.

The reaction mixture was then quenched into 3M hydrochloric acid (100 ml) and the residual THF stripped under vacuum. The resulting aqueous layer was backwashed with ethyl acetate (2×100 ml) at which point a fine yellow precipitate of the beta-diketone formed in the aqueous, and was isolated by filtration.

The resulting wet β-diketone, (2.02 g) was then cyclised to 8-amino-4-oxo-2-(tetrazol-5-yl)-4H-1-benzopyran by slurrying in (50 ml) of refluxing methanol containing (0.6 ml) of concentrated hydrochloric acid for 2 hours. The resulting yellow precipitate was cooled to 5° C., filtered and dried for 18 hrs at 50° C. under vacuo (300–400 mm Hg) to give pure 8-amino-4-oxo-2-(tetrazol-5-yl)-4H-1-benzopyran (0.45 g, 41.3%) as a yellow powder.

Mp: decomposes above 280° C. IR (nujol): 3450, 3337, 1631, 1606, 1597, 1583, 1534, 1496, 1377, 1365, 1327, 1066, 880, 866, 806, 751 $cm^{-1}$. m/z=230 [M+H]+, 202, 187, 157, 136, 129, 91.

Method B

A solution of the sodium salt of ethyl tetrazole-5-carboxylate (2.65 g, 16.1 mmol) in DMF (10 ml) was added to a mixture of 3-amino-2-hydroxyacetophenone (1.87 g, 12.4 mmol) and potassium t-butoxide (6.96 g, 62.0 mmol) in DMF (20 ml). The reaction mixture was stirred at 0–5° C. for 40 minutes. Methanol (30 ml) and conc. hydrochloric acid (10 ml) were added and the mixture was heated at reflux. After 90 minutes the reaction mixture was cooled and filtered. The filter cake was washed with 3:1 methanol-water and then with water. The product was dried at 20° C. to give 8-(carboxytetrazol-5-yl) amino-4-oxo-2(tetrazol-5-yl)-4H-11-benzopyran (0.55 g, 14%) as an off-white solid. m/z=326 [M+H]+, 270, 228, 213, 201, 185, 157.

The filtrate was diluted to about 300ml with water and allowed to stand for 18 hours whereupon a yellow precipitate formed. The precipitate was filtered off, washed with water and dried at 20° C. to give 8-amino-4-oxo-2(tetrazol-5-yl)-4H-1-benzopyran (0.58 g, 20%) identical to the product obtained by method A. m/z: 230 [M+H]+, 202, 187, 157, 136, 129, 91.

EXAMPLE 2

Preparation of 4-oxo-8-[4-(4-phenylbutoxy) benzoylamino]-2-(tetrazol-5-yl)-4H-1-benzopyran Methanesulphonyl chloride (2.7 ml, 1.6 eq) was added to a stirred suspension of disodium tetrazole-5-carboxylate (5.0 g, 1.4 eq) in DMF (75 ml) at ambient temperature under a blanket of nitrogen. The mixture was stirred for 2 h at ambient temperature, then treated with pyridine (10 ml, 5.7 eq) followed by 3-[4-(phenylbutoxy)benzoylamino]-2-hydroxyacetophenone (9.0 g, 1.0 eq). The resulting reaction mixture was quenched with 2M aqueous hydrochloric acid. The intermediate phenyl ester was extracted into ethyl acetate, the organic layer washed, dried and evaporated to give the crude phenyl ester in 90% conversion (estimated by ¹H NMR spectroscopy). A solution of the crude phenol ester (2.0 g, 1.0 eq) in DMF (5 ml) was added dropwise to a stirred solution of potassium tert-butoxide (2.0 g, 4.0 eq) in DMF (10 ml) at about 5° C. under a blanket of nitrogen. The resulting mixture was stirred at about 5° C. for 45 min, then quenched into 2M aqueous hydrochloric acid. The required β-diketone was isolated in 50% yield by filtration, washed with water and dried in vacuo. The crude β-diketone (0.3 g, 1.0 eq) was suspended in methanol (3 ml), treated with concentrated sulphuric acid (0.2 ml) and the resulting mixture was heated at reflux for 5 h. The reaction mixture was cooled, filtered, washed and the solid dried to give 4-oxo-8-[4-(4-phenylbutoxy)benzoylamino]-2-(tetrazol-5-yl)-4H-1-benzopyran in 77% yield. The product was identified by HPLC comparison with an authentic sample.

We claim:

1. A process for the preparation of a compound of structure (I):

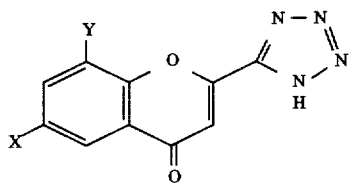 (I)

in which Y is NO₂, NH₂ or a protected amine group; and X is hydrogen or halogen, which process comprises cyclisation of a compound of structure (II):

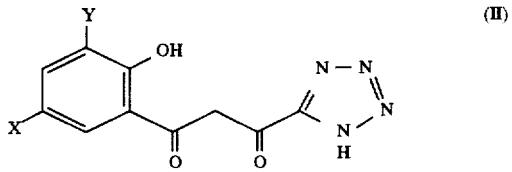 (II)

in which X and Y are as described for structure (I) by refluxing a compound of structure (II) in a $C_{1-4}$ alkanol solvent in the presence of a suitable acid.

2. A compound of structure (II) as described in claim 1.

3. The process of claim 1 wherein the process is carried out at reflux temperature in methanol in the presence of concentrated hydrochloric acid or concentrated sulphuric acid.

* * * * *